(12) United States Patent
Horvath

(10) Patent No.: US 8,426,469 B2
(45) Date of Patent: Apr. 23, 2013

(54) CRYSTALLINE LEUKOTRIENE $B_4$

(75) Inventor: Karol Horvath, Södertälje (SE)

(73) Assignee: LTB4 Sweden AB, Stockholm (SE)

( * ) Notice: Subject to any disclaimer, the term of this patent is extended or adjusted under 35 U.S.C. 154(b) by 184 days.

(21) Appl. No.: 12/295,065

(22) PCT Filed: Mar. 30, 2007

(86) PCT No.: PCT/EP2007/053084
§ 371 (c)(1),
(2), (4) Date: Mar. 9, 2009

(87) PCT Pub. No.: WO2007/113239
PCT Pub. Date: Oct. 11, 2007

(65) Prior Publication Data
US 2009/0281185 A1    Nov. 12, 2009

(30) Foreign Application Priority Data
Mar. 30, 2006  (EP) .................... 06112011

(51) Int. Cl.
*A61K 31/202* (2006.01)
*C07C 59/42* (2006.01)
(52) U.S. Cl.
USPC ......................... 514/560; 554/219

(58) Field of Classification Search .......... 514/560; 554/219
See application file for complete search history.

(56) References Cited

U.S. PATENT DOCUMENTS
4,873,024 A    10/1989   Abe et al.
2006/0063837 A1*  3/2006  Borgeat .......... 514/560

FOREIGN PATENT DOCUMENTS
EP    1 840 114 A1    10/2007
WO    WO 2007/113239 A1    10/2007

OTHER PUBLICATIONS

Francis A. J. Kerdesky et al., "Total Synthesis of Leukotriene B4", J. Org Chem. 1993, vol. 58, No. 13, 1993, 3516-3520.
Yuichi Kobayashi et al., "Highly Stereocontrolled Total Synthesis of Leukotriene B4, 20-Hydroxyleukotriene B4, Leukotriene B3, and Their Analogues", J. Org. Chem. 1990, 55, 5324-5335.

* cited by examiner

*Primary Examiner* — Sreeni Padmanabhan
*Assistant Examiner* — Sahar Javanmard
(74) *Attorney, Agent, or Firm* — Foley & Lardner LLP

(57) ABSTRACT

Leukotriene $B_4$, 5S,12R-dihydroxy-6,8,10,14(Z,E,E,Z)-eicosatetraenoic acid, is a twenty carbon tetra-unsaturated fatty acid. No crystal forms of leukotriene $B_4$ ($LTB_4$) are known in the art. The present inventors have discovered a crystal form of $LTB_4$ and the present invention therefore relates to crystal forms of $LTB_4$ in general, and the novel crystal form A of $LTB_4$ in particular.

2 Claims, 3 Drawing Sheets

CRYSTALLINE LEUKOTRIENE $B_4$

FIELD OF THE INVENTION

The present invention relates to leukotriene $B_4$ and crystal forms thereof. The present invention furthermore relates to pharmaceutical formulations of said crystalline leukotriene $B_4$.

BACKGROUND OF THE INVENTION

Leukotriene $B_4$, 5S,12R-dihydroxy-6,8,10,14(Z,E,E,Z)-eicosatetraenoic acid, is a twenty carbon tetra-unsaturated fatty acid and is a relatively unstable molecule. Isotonic aqueous solutions of leukotriene $B_4$ (LTB4) at pH 7.0-7.6, which are suitable for administration to humans and animals are stable for only short periods of time (weeks to months) when stored at temperatures ranging from 2° C. to 25° C. (and above 25° C.). Indeed, $LTB_4$ agents are subject to oxidation, isomerization of double bounds ($LTB_4$ contains two cis and two trans double bounds), epimerization ($LTB_4$ contains two chiral centers), esterification ($LTB_4$ contains a carboxylic group), lactonization, among various possible structural alterations.

$LTB_4$ agents have great pharmaceutical utility, but their use as therapeutic agents in animals or human is problematic, because of their insufficient stability and shelf-life in solution at temperatures between 2° C. to 25° C.

No formulations of solid $LTB_4$ have been reported. Indeed, free $LTB_4$ is known in the art to be an oily substance at room temperature (Kerdesky et al., *J. Org. Chem.*, Vol. 58, 1993, 3516-3520, and U.S. Pat. No. 4,873,024). Kobayashi et al., *J. Org. Chem.*, Vol. 55, 1990, 5324-5335, report a melting point of 25-28° C. for solid leukotriene $B_4$. Crystalline $LTB_4$ has not been reported in the art and no suggestion has been provided of a solid form of $LTB_4$ suitable for solid formulations.

Given the potential of $LTB_4$ agents as therapeutic agents for the prophylaxis and treatment of infections and cancer in humans and animals, it would be highly desirable to provide a novel form of $LTB_4$ suitable for solid pharmaceutical formulations.

SUMMARY OF THE INVENTION

The inventors of the present invention have surprisingly found a novel crystalline form of $LTB_4$ that has a melting point as high as 79° C. Accordingly, one aspect of the invention concerns leukotriene $B_4$ in a crystalline form, or a hydrate thereof. The high melting point of the novel crystalline form of leukotriene $B_4$ provides a particular advantage over the prior art for formulating pharmaceutical compositions of leukotriene $B_4$. Another aspect of the invention concerns a composition comprising crystalline leukotriene $B_4$, or a hydrate thereof, and a pharmaceutically acceptable carrier.

A third aspect of the invention concerns said crystal forms of leukotriene $B_4$ or said compositions thereof for use as a medicament.

DETAILED DESCRIPTION OF THE INVENTION

The inventors of the present invention have surprisingly found that leukotriene $B_4$ may be crystallized from several solvent alternatives. Therefore, in one aspect, the present invention concerns crystalline leukotriene $B_4$, 5S,12R-dihydroxy-6,8,10,14(Z,E,E,Z)-eicosatetraenoic acid, or a hydrate thereof.

Figure 1:
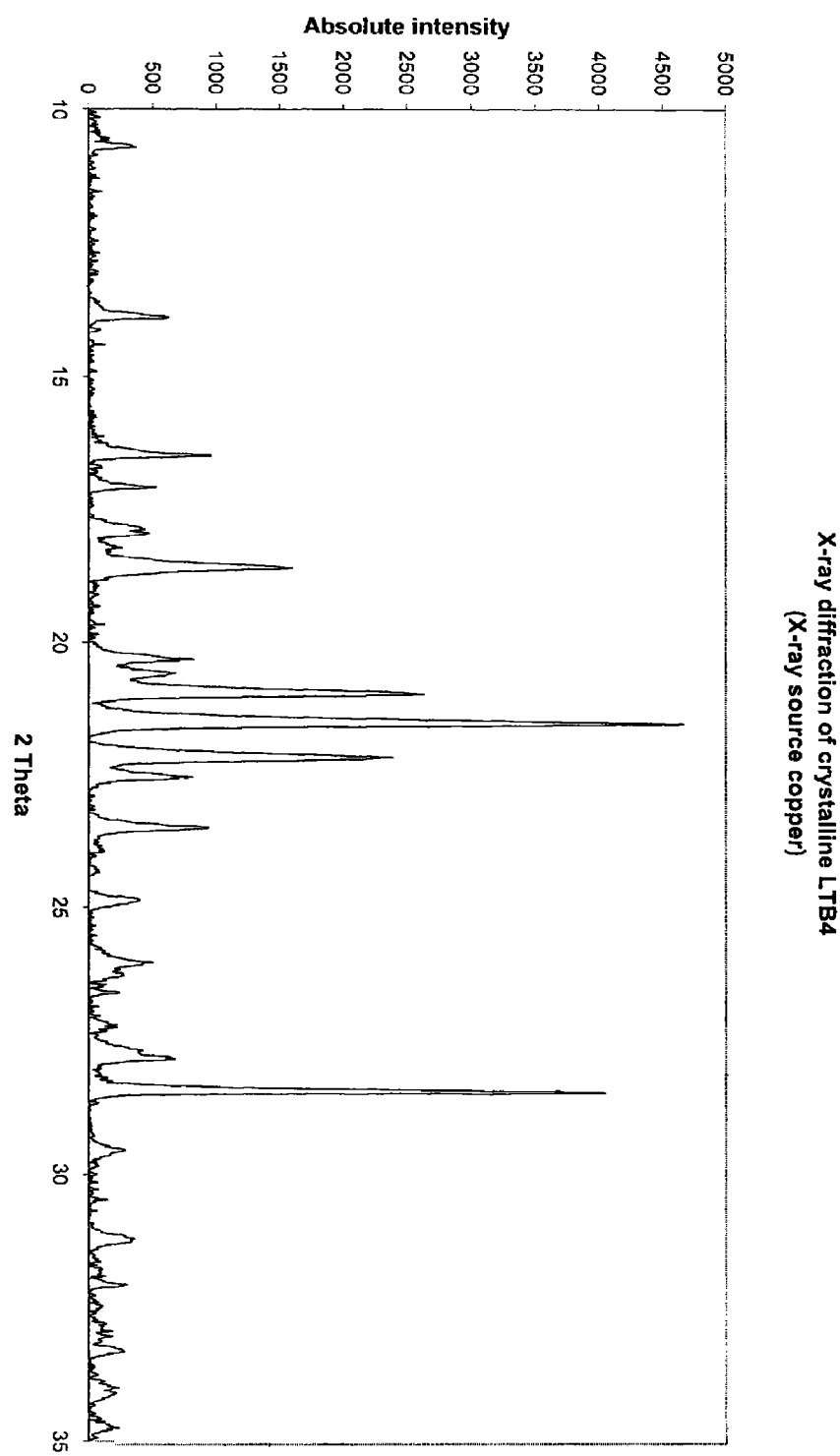
FIG. 1 is a diffractogram of crystalline form A of leukotriene $B_4$, obtained using copper as an X-ray source.

The X-ray powder diffractogram of one form of crystalline leukotriene $B_4$, referred to in the context of the present invention as Form A, is shown in FIG. 1. The data have been obtained with copper as an X-ray source and the most significant peaks are found at 18.6±0.2, 21.0±0.2, 21.5±0.2, 22.2±0.2 and 23.5±0.2 degrees two-theta (2θ). Accordingly, one embodiment relates to leukotriene $B_4$ Form A, which is characterized by X-ray powder diffraction peaks at 18.6±0.2, 21.0±0.2, 21.5±0.2, 22.2±0.2 and 23.5±0.2 degrees two-theta with copper as an X-ray source, or a hydrate thereof. In a preferred embodiment, the leukotriene $B_4$ Form A is characterized by a powder X-ray diffraction pattern as substantially depicted in FIG. 1. The intensity of the peaks may vary according to the method of measurement and the signal to noise ratio may also vary, but the angle of the peaks will only vary within the boundaries set by the measurement uncertainties of the equipment used for the measurements.

Depending on the wavelength of the X-rays, i.e. depending on the source of the X-rays, the scattering angle may vary. Hence, Form A may also be characterized by the peaks in a diffractogram obtained with chromium as an X-ray source. Accordingly, an alternative embodiment of the invention relates to leukotriene $B_4$ Form A, which is characterized by X-ray powder diffraction peaks at 8.8±0.2, 10.7±0.2, 31.4±0.2, 32.2±0.2 and 33.2±0.2 degrees two-theta with chromium as an X-ray source, or a hydrate thereof. In a preferred embodiment, the leukotriene $B_4$ Form A is characterized by a powder X-ray diffraction pattern as substantially depicted in FIG. 2. The intensity of the peaks may vary according to the method of measurement and the signal to noise ratio may also vary, but the angle of the peaks will only vary within the boundaries set by the measurement uncertainties of the equipment used for the measurements.

The dimensions of the unit cell of leukotriene $B_4$ Form A may be calculated on the basis of the X-ray data. The inventors have found the following unit cell dimensions:

a=16.14±0.01 Angstrom b=5.15±0.01 Angstrom c=13.79±0.01 Angstrom

In one embodiment the present invention relates to crystalline Form A of leukotriene $B_4$ having unit cell dimensions of a=16.14±0.01 Angstrom, b=5.15±0.01 Angstrom and c=13.79±0.01 Angstrom.

Figure 3:
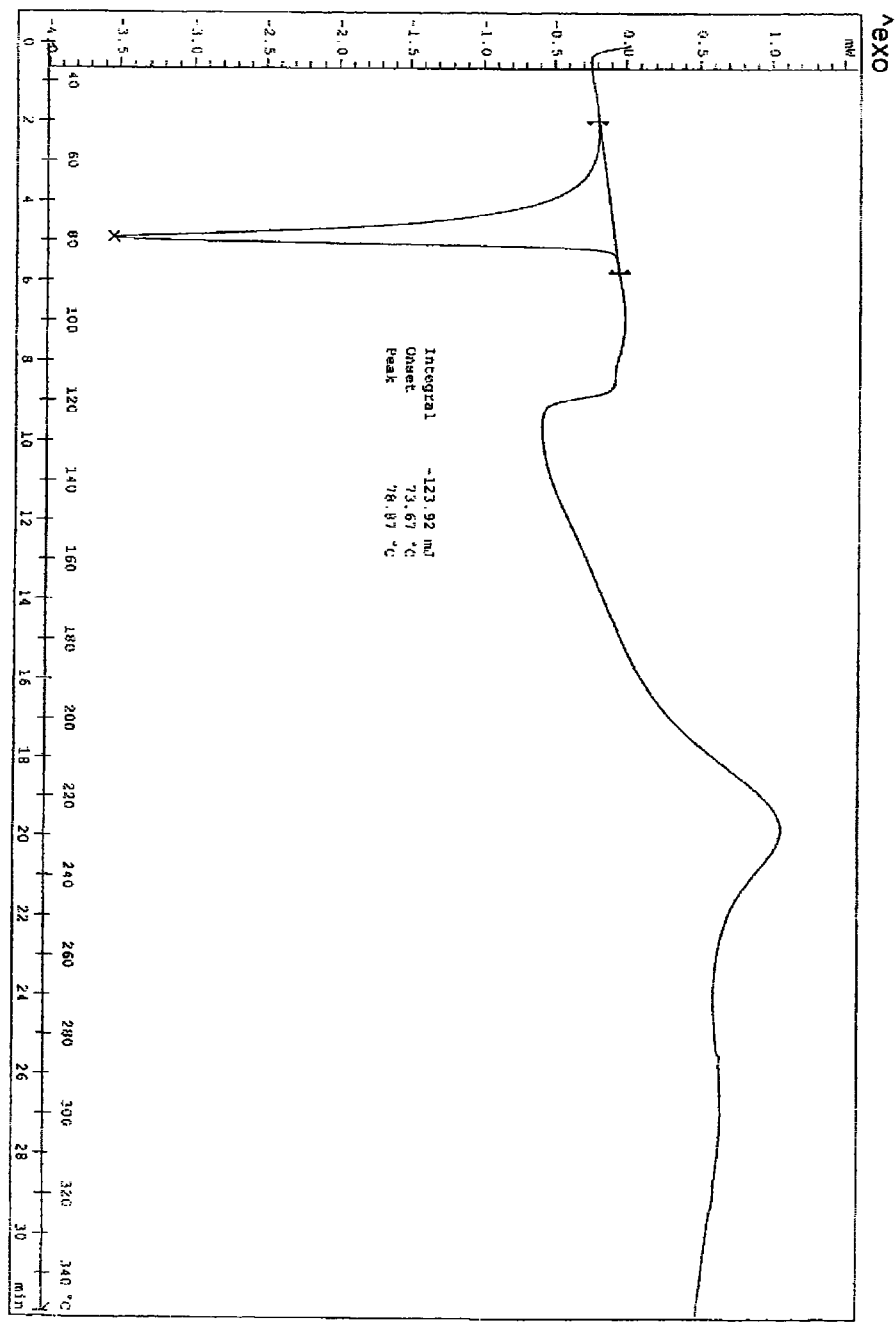
FIG. 3 is a DSC thermogram of crystalline form A of leukotriene $B_4$, wherein the scan has been performed from 30 to 350° C.

Another characteristic of the novel crystalline forms is their high melting temperature. More specifically, a leukotriene $B_4$ crystal may be characterized by Differential Scanning Calorimetry (DSC). FIG. 3 shows a DSC thermogram for leukotriene $B_4$ Form A. The endothermic phase transition peaks at about 79° C. Therefore, in one embodiment, the present invention relates to leukotriene $B_4$ Form A having a peak in the range 75 to 85° C. in a DSC thermogram, preferably in the range 77 to 81° C., more preferably around 79° C., or a hydrate thereof. The peak in FIG. 3 is quite wide. The width of the peak, without being bound by a particular theory, could be due to thermal decomposition of the relatively unstable $LTB_4$. In this particular example, the onset of said peak is at about 74° C.

As mentioned above, the novel crystalline forms of leukotriene $B_4$ provide advantages in formulating pharmaceutical compositions, in particular solid compositions. Accordingly, one aspect of the present invention relates to a pharmaceutical composition comprising the leukotriene $B_4$ in crystalline form, or a hydrate thereof, and a pharmaceutically acceptable carrier. In a preferred embodiment, the composition according to the present invention comprises leukotriene $B_4$ Form A as described above, or a hydrate thereof, and a pharmaceutically acceptable carrier.

The expression "pharmaceutically acceptable carrier", in the context of the present invention, is intended to include any carrier suitable for physiological and pharmaceutical usage. Such carrier is selected from the group consisting of water, buffered salt solutions, such as phosphate buffered saline (PBS), or sodium chloride solutions buffered with agents such as Tris, glycine or other amino acids, in particular basic amino acids, aqueous solution containing alcohol, such as ethanol, propylenglycol, propanediol, glycerol, or mannitol, as well as sugar solutions, such as glucose or lactose solutions, or a mixture of the various solvents mentioned. Furthermore, the expression "pharmaceutically acceptable carrier" may include inert diluents or fillers, such as sucrose, sorbitol, sugar, mannitol, microcrystalline cellulose, starches including potato starch, calcium carbonate, sodium chloride, lactose, calcium phosphate, calcium sulfate or sodium phosphate; granulating and disintegrating agents, for example, cellulose derivatives including microcrystalline cellulose, starches including potato starch, croscarmellose sodium, alginates or alginic acid; binding agents, for example, sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone or polyethylene glycol; and lubricating agents, including glidants and antiadhesives, for example, magnesium stearate, zinc stearate, stearic acid, silicas, hydrogenated vegetable oils or talc.

It was furthermore found that leukotriene $B_4$ is more stable at alkaline pH than at neutral or acidic pH. Accordingly, in a preferred embodiment, the composition according to the present invention comprises an alkaline reacting carrier. The expression "alkaline reacting carrier", in the context of the present invention, is intended to include an otherwise inert, pharmaceutically acceptable substance (or substances), which creates an alkaline "micro-pH" between 8.2 and 14, especially between 8.5 and 12.5, such as between 8.5 and 11.5, most preferably between 9.5 and 11.5, such as about 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, or 11.5, around each $LTB_4$ particle when water is adsorbed to the particles of the mixture or when water is added in small amounts to the mixture. In another preferred embodiment, the alkaline "micro-pH" ranges between 8.0 and 9.0, between 8.5 and 9.5, between 9.0 and 10.0, or between 10.0 and 11.5. Such substances creating said "micro-pH" can be chosen among, but are not restricted to substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances, such as $Al_2O_3.6MgO.CO_2.12H_2O$, $(Mg_6Al_2(OH)_{16}CO_3.4H_2O)$, $MgO.Al_2O_3.2SiO_2.nH_2O$ or similar compounds; organic pH-buffering substances such as trihydroxymethylaminomethane or other similar, pharmaceutically acceptable pH-buffering substances.

Any suitable type or mode of administration may be employed for providing a mammal, especially a human with an effective dosage of $LTB_4$. For example, oral, parenteral, intraduodenal, intrajejunal and topical may be employed. Dosage forms include tablets, capsules, powders, solutions, dispersions, suspensions, creams, ointments and aerosols.

In a preferred embodiment, the compositions of the present invention may be in an oral dosage form with an enteric coating. From the statement about the stability properties of $LTB_4$ above, it is obvious that it is advantageous that an oral dosage form of the said crystalline $LTB_4$ must be protected from contact with the acidic gastric juice in order to reach the small intestine without degradation.

The enteric coated preparations are resistant to dissolution in acid media and dissolve rapidly in neutral to alkaline media. The enteric coated dosage form is preferably characterized in the following way. Cores containing the crystalline $LTB_4$ mixed with alkaline reacting compounds are coated with two or more layers, in which the first layer/layers is/are soluble in water or rapidly disintegrating in water and consist(s) of non-acidic, otherwise inert pharmaceutically acceptable substances. This/these first layer/layers separates/separate the alkaline reacting core material from the outer layer, which is an enteric coating. The final, enteric coated dosage form is treated in a suitable way to reduce the water content to a very low level in order to obtain a good stability of the dosage form during long-term storage.

The crystalline $LTB_4$ is mixed with inert, preferably water soluble, conventional pharmaceutical constituents to obtain the preferred concentration of the active compound in the final mixture and with an alkaline reacting, otherwise inert, pharmaceutically acceptable substance (or substances), which creates a "micro-pH" as defined above, when water is adsorbed to the particles of the mixture or when water is added in small amounts to the mixture. Such substances can be chosen among substances such as the sodium, potassium, calcium, magnesium and aluminium salts of phosphoric acid, carbonic acid, citric acid or other suitable weak inorganic or organic acids; substances normally used in antacid preparations such as aluminium, calcium and magnesium hydroxides; magnesium oxide or composite substances such as $Al_2O_3.6MgO$ $CO_2.12H_2O$, $(Mg_6Al_2(OH)_{16}CO_3$ $4H_2O)$, $MgO.Al_2O_3.2SiO_2.nH_2O$, wherein n is not an integer and less than 2, or similar compounds; organic pH-buffering substances such as trishydroxymethylaminomethane or other similar, pharmaceutically acceptable pH-buffering substances.

The powder mixture is then formulated into small beads i.e. pellets or tablets, by conventional pharmaceutical procedures. The pellets or tablets are used as cores for further processing.

The alkaline reacting cores containing the crystalline $LTB_4$ must be separated from the enteric coating polymer(s) containing free carboxyl groups, which otherwise causes degradation of the crystalline $LTB_4$ during the coating process or during storage. The subcoating layer, (the separating layer), also serves as a pH-buffering zone in which hydrogen ions diffusing from the outside in towards the alkaline core can react with hydroxyl ions diffusing from the alkaline core towards the surface of the coated particles. The pH-buffering properties of the separating layer can be further strengthened by introducing in the layer substances chosen from a group of compounds usually used in antacid formulations such as, for instance, magnesium oxide, hydroxide or carbonate, aluminium or calcium hydroxide, carbonate or silicate; composite aluminium/magnesium compounds such as, for instance $Al_2O_3.6MgO$ $CO_2.12H_2O$, $(Mg_6Al_2(OH)_{16}CO_3,4H_2O)$, $MgO.Al_2O_3.2SiO_2.nH_2O$, wherein n is not an integer and less than 2, or similar compounds; or other pharmaceutically acceptable pH-buffering substances such as, for instance the sodium, potassium, calcium, magnesium and aluminium salts of phosphoric, citric or other suitable, weak, inorganic or organic acids.

The separating layer consists of one or more water soluble inert layers, optionally containing pH-buffering substances.

The separating layer(s) can be applied to the cores—pellets or tablets—by conventional coating procedures in a suitable coating pan or in a fluidized bed apparatus using water and/or conventional organic solvents for the coating solution. The material for the separating layer is chosen among the pharmaceutically acceptable, water soluble, inert compounds or polymers used for film-coating applications such as, for instance sugar, polyethylene glycol, polyvinylpyrollidone, polyvinyl alcohol, hydroxypropyl cellulose, hydroxymethyl cellulose or hydroxypropyl methylcellulose. The thickness of the separating layer is not less than 2 µm, for small spherical pellets preferably not less than 4 µm, for tablets preferably not less than 10 µm.

In the case of tablets another method to apply the coating can be performed by the drycoating technique. First a tablet containing the acid labile compound is compressed as described above. Around this tablet another layer is compressed using a suitable tableting machine. The outer, separating layer, consists of pharmaceutically acceptable, in water soluble or in water rapidly disintegrating tablet excipients. The separating layer has a thickness of not less than 1 mm. Ordinary plasticizers, pigments, titanium dioxide talc and other additives may also be included into the separating layer.

The enteric coating layer is applied on to the sub-coated cores by conventional coating techniques such as, for instance, pan coating or fluidized bed coating using solutions of polymers in water and/or suitable organic solvents or by using latex suspensions of said polymers. As enteric coating polymers can be used, for example, cellulose acetate phthalate, hydroxypropyl methylcellulose phthalate, polyvinyl acetate phthalate, co-polymerized methacrylic acid/methacrylic acid methyl esters such as, for instance, compounds known under the trade name Eudragit® L 12,5 or Eudragit® L 100, (Röhm Pharma) or similar compounds used to obtain enteric coatings.

The enteric coating can also be applied using water-based polymer dispersions, e.g. Aquateric (FMC Corporation), Eudragit® L 100-55 (Röhm Pharma), Coating CE 5142 (BASF). The enteric coating layer can optionally contain a pharmaceutically acceptable plasticizer such as, for instance, cetanol, triacetin, citric acid esters such as, for instance, those known under the trade name Citroflex® (Pfizer) phthalic acid esters, dibutyl succinate or similar plasticizers.

The amount of plasticizer is usually optimized for each enteric coating polymer(s) and is usually in the range of 1-20% of the enteric coating polymer(s). Dispersants such as talc, colourants and pigments may also be included into the enteric coating layer.

Thus, the enteric coated preparation according to the invention consists of cores containing the crystalline $LTB_4$ mixed with an alkaline reacting compound. The cores are coated with a water soluble or in water rapidly disintegrating coating, optionally containing a pH-buffering substance, which separates the alkaline cores from the enteric coating. The sub-coated dosage form is finally coated with an enteric coating rendering the dosage form insoluble in acid media, but rapidly disintegrating/dissolving in neutral to alkaline media such as, for instance the liquids present in the proximal part of the small intestine, the site where dissolution is wanted.

$LTB_4$ has high potential as a therapeutic agent for the prophylaxis and treatment of infections and cancer in humans and animals. Accordingly, in another aspect, the invention relates to crystalline leukotriene $B_4$ according to the present invention or the pharmaceutical composition according to the present invention for use as a medicament.

EXAMPLES

The present invention will be further illuminated in the following, non-limiting examples.
Methods
Conditions for obtaining X-ray Powder Diffraction (XRPD) patterns:

| | |
|---|---|
| Registration: | Photographic recording using a Guinier Hägg camera, corrected radius 50.1247 mm for Cu and corrected radius 50.0330 mm for Cr. |
| X-Ray source: | Strictly monochromatic $CuK\alpha_1$-radiation ($\lambda = 1.5405$ Å) and $CrK\alpha_1$-radiation ($\lambda = 2.28975$ Å), Instrumenttjänst AB, Sweden. |
| Evaluation: | Automatic laser scanner, University of Stockholm. |

Conditions for obtaining Differential Scanning Calorimetry (DSC) thermograms:

| | |
|---|---|
| Instrument: | $DSC/822^e$ Mettler Toledo |
| Software: | Mettler Toledo $Star^e$ System |
| Temperature range: | 30.0 to 350.0° C. |
| Rate: | 10.00° C./min |
| $N_2$-flow: | 80.0 mL/min |

Example 1

Synthesis of Form A Crystals

Leukotriene $B_4$ in ethanol solution (1.5% w/w) from Cascade Biochem Ltd. (Stock No: 31350, Lot. No:3468.B.05.1) was concentrated to dryness affording an oily residue, which was re-dissolved in t-butyl-methyl ether. Heptane was added at −70° C. to afford a colourless emulsion containing a small amount of precipitate. The emulsion was isolated and after about 10 minutes at room temperature a thin slurry with white crystalline precipitate was observed under a light microscope. The slurry was cooled to 0° C. and became thicker. The crystals were filtered off and dried at room temperature. The crystals were fibre-like with a thickness of less than 5 µm and a length of 40-80 µm.
Variation of Solvents It was found that a variation of different solvents could be used for obtaining the crystals. In general it was found that addition of an anti-solvent (solvent wherein $LTB_4$ is only slightly soluble or insoluble) to a solution of $LTB_4$ would provide a crystalline precipitate. Table 1 below summarizes the solubility of $LTB_4$ in various solvents.

TABLE 1

| Very soluble | Slightly soluble or insoluble |
|---|---|
| Methanol | Toluene |
| Ethanol | Water |
| Isopropyl alcohol | Heptane |
| Acetone | |
| Methyl isobutyl ketone | |
| Ethyl acetate | |
| Isopropyl acetate | |

TABLE 1-continued

| Very soluble | Slightly soluble or insoluble |
|---|---|
| | Acetonitrile |
| | t-butyl-methyl ether |
| | Dichloromethane |
| | Tetrahydrofuran |

It is envisioned that any combination of a solvent from the left column in combination with a solvent from the right column will result in a crystalline precipitate. In particular solvent combinations selected from the group consisting of ethanol/water, t-butyl-methyl ether/heptane, t-butyl-methyl ether/toluene, acetone/toluene, ethanol/toluene, isopropyl alcohol/toluene and tetrahydrofuran/toluene, which have all been shown to provide $LTB_4$ crystals in a manner similar to the process described for t-butyl-methyl ether/heptane above, are contemplated as being part of the present invention.

Characterization of the Crystals

A diffractogram with Cu as an X-ray source performed on crystals obtained from ethanol/water is shown in FIG. 1. The two-theta values corresponding to FIG. 1 are summarized in Table 2:

TABLE 2

| Cu radiation | Cr radiation |
|---|---|
| 10.703 | 8.774 |
| 13.895 | 10.277 |
| 14.408 | 10.669 |
| 16.474 | 15.923 |
| 17.078 | 20.683 |
| 17.859 | 21.478 |
| 17.951 | 24.574 |
| 18.210 | 25.493 |
| 18.585 | 26.619 |
| 20.317 | 26.790 |
| 20.582 | 27.216 |
| 20.949 | 27.768 |
| 21.513 | 30.403 |
| 22.161 | 30.825 |
| 22.539 | 31.367 |
| 23.497 | 31.967 |
| 23.915 | 32.208 |
| 24.306 | 33.223 |
| 24.861 | 33.782 |
| 26.043 | 35.254 |
| 26.241 | 35.833 |
| 26.596 | 36.498 |
| 27.197 | 37.358 |
| 27.695 | 38.068 |
| 27.825 | 38.861 |
| 28.446 | 39.158 |
| 29.552 | 39.465 |
| 31.216 | 39.987 |
| 32.071 | |
| 33.312 | |
| 33.997 | |
| 34.100 | |
| 34.740 | |

Figure 2:
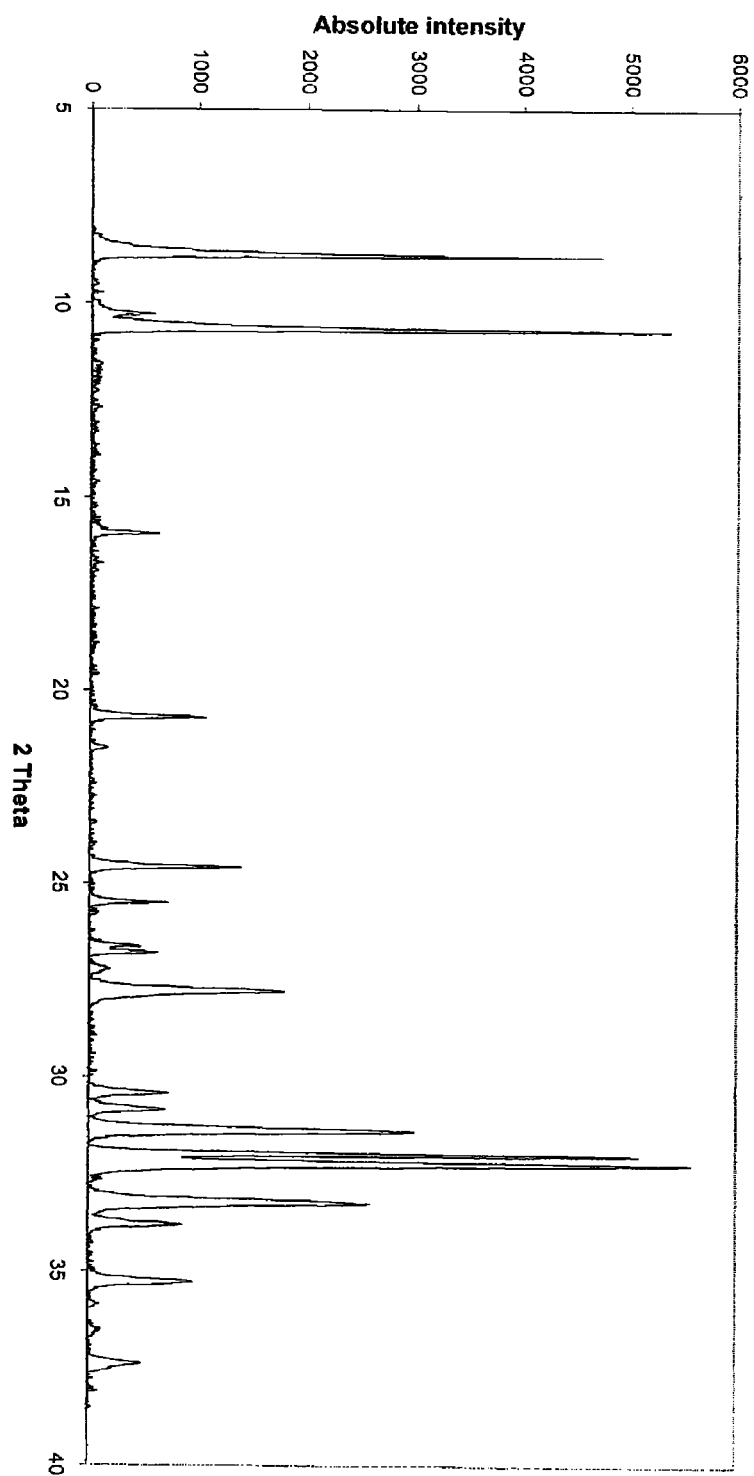
FIG. 2 is a diffractogram of crystalline form A of leukotriene $B_4$, obtained using chromium as an X-ray source.

A diffractogram with Cr as an X-ray source is shown for the same crystals in FIG. 2. The two-theta values corresponding to FIG. 2 are also summarized in Table 2.

A DSC thermogram for the crystals obtained from ethanol/water is shown in FIG. 3.

The invention claimed is:
1. Leukotriene $B_4$ Form A, which is characterized by
   (A) X-ray powder diffraction peaks at 18.6±0.2, 21.0±0.2, 21.5±0.2, 22.2±0.2 and 23.5±0.2 degrees two-theta with copper as an X-ray source, and X-ray powder diffraction peaks at 8.8±0.2, 10.7±0.2, 31.4±0.2, 32.2±0.2 and 33.2±0.2 degrees two-theta with chromium as an X-ray source, and
   (B) a peak in the range 75 to 85° C. in a DSC thermogram.
2. A solid pharmaceutical composition comprising the leukotriene $B_4$ Form A according to claim 1 and a pharmaceutically acceptable carrier.

* * * * *